US00PP16894P2

(12) United States Plant Patent

Pellett

(10) Patent No.: US PP16,894 P2

(45) Date of Patent: Jul. 25, 2006

(54) *PHYSOCARPUS* PLANT NAMED 'CENTER GLOW'

(50) Latin Name: *Physocarpus opulifolius*
Varietal Denomination: Center Glow

(76) Inventor: Harold M. Pellett, 1450 Game Farm Rd. N., Mound, MN (US) 55364

( * ) Notice: Subject to any disclaimer, the term of this patent is extended or adjusted under 35 U.S.C. 154(b) by 5 days.

(21) Appl. No.: 11/130,664

(22) Filed: May 17, 2005

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent Bell
*Assistant Examiner*—Annette H Para
(74) *Attorney, Agent, or Firm*—Penny J. Aguirre

(57) ABSTRACT

A new cultivar of *Physocarpus, Physocarpus opulifolius* 'Center Glow', characterized by its upright, mounded habit, and its unique foliage with leaves that emerge bright purple red with bright gold and develop to a bright but slightly darker purple red.

2 Drawing Sheets

Genus/species: *Physocarpus opulifolius.*
Varietal denomination: 'Center Glow'.

BACKGROUND OF THE INVENTION

The present invention relates to a new and distinct cultivar of *Physocarpus opulifolius* and will be referred to hereafter by its cultivar name, 'Center Glow'. 'Center Glow' represents a new cultivar of *Physocarpus*, a deciduous shrub grown for landscape use.

The new *Physocarpus* arose from a breeding program conducted by the inventor at a trial site in Mound, Minn. The objective of the breeding program was to develop new *Physocarpus* cultivars with superior foliage color.

The new *Physocarpus* originate from a cross-pollination made by the inventor in summer of 2001. The female parent was *Physocarpus opulifolius* 'monlo' (U.S. Plant Pat. No. 11,211) and the male parent was *Physocarpus opulifolius* 'Dart's Gold' (Not patented). 'Center Glow' was selected as a single plant from a population of progeny derived from the cross-pollination in Mound, Minn. in summer of 2002.

'Center Glow' was selected as unique for its bright red purple foliage with a bright gold region near the base of the newly emerging leaves and bright red purple mature foliage. The foliage of the female parent 'monlo' is darker, is more purple in color, and the base of the emerging leaves is green in color. The foliage of the male parent, 'Dart's Gold' is yellow to gold.

Asexual reproduction of the new cultivar was first accomplished by stem cuttings at the University of Minnesota Horticultural Research Center in Chaska, Minn. in summer of 2002 by the inventor. The characteristics of this cultivar have been determined to be stable and are reproduced true to type in successive generations.

SUMMARY OF THE INVENTION

The following traits have been repeatedly observed and represent the characteristics of the new *Physocarpus*. These attributes in combination distinguish 'Center Glow' as unique and distinct from all other cultivars of *Physocarpus* known to the inventor.

1. The foliage of 'Center Glow' has leaves that emerge bright red with a gold region near the base, gradually changes to a darker purple red as the season progresses.
2. The plant habit of 'Center Glow' is upright and mounding with dense foliage.
3. 'Center Glow' propagated readily from stem cutting to form well-developed fibrous root system.
4. 'Center Glow' flowers with white flowers in early summer, with flowers similar to the parental cultivars.

BRIEF DESCRIPTION OF THE DRAWING

The accompanying photographs were taken of a two year-old plants of 'Center Glow' as grown outdoors under full sun in Mound, Minn. and are representative of the of the new *Physocarpus*.

The photograph in FIG. 1 was taken in June and is representative of a typical plant of 'Center Glow'.

Figure 1:
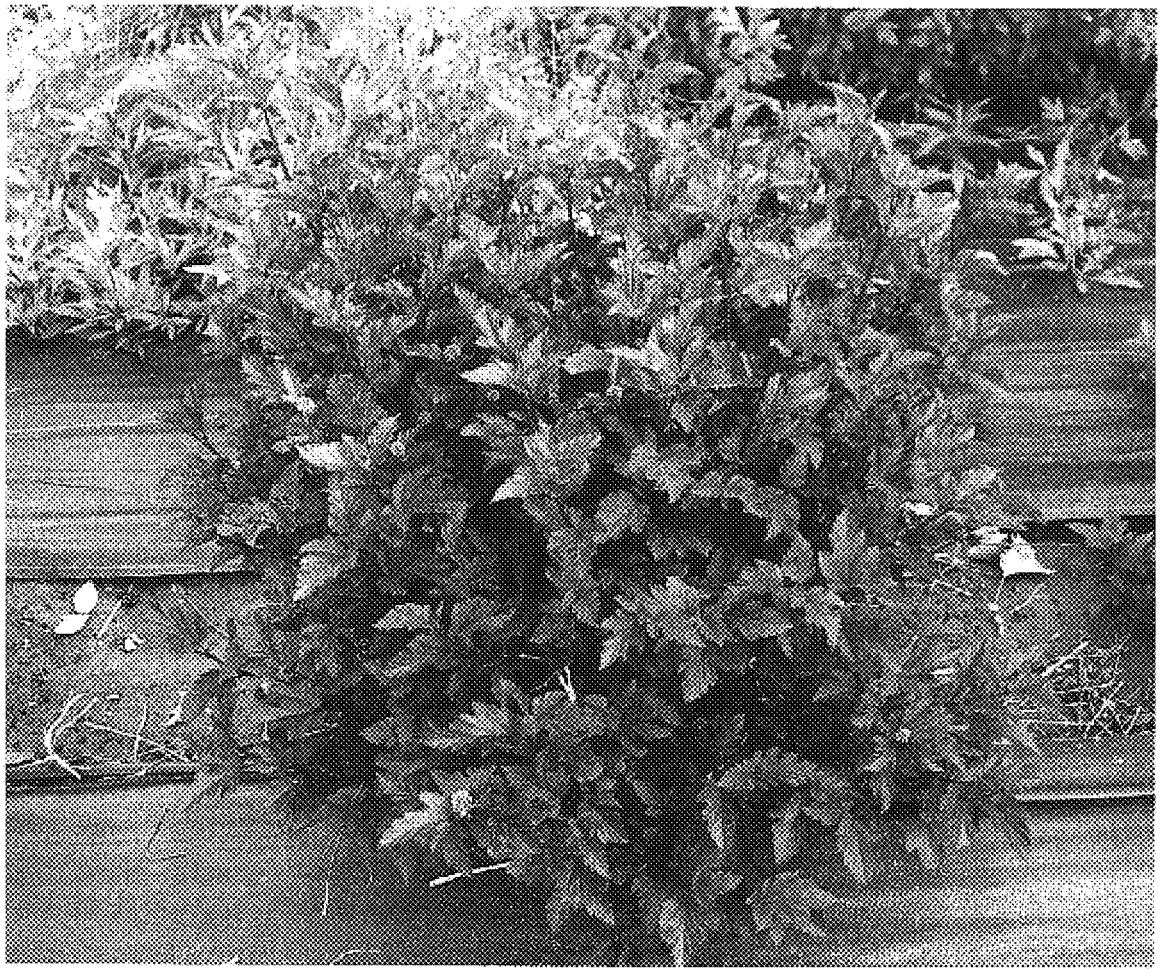
Figure 2:
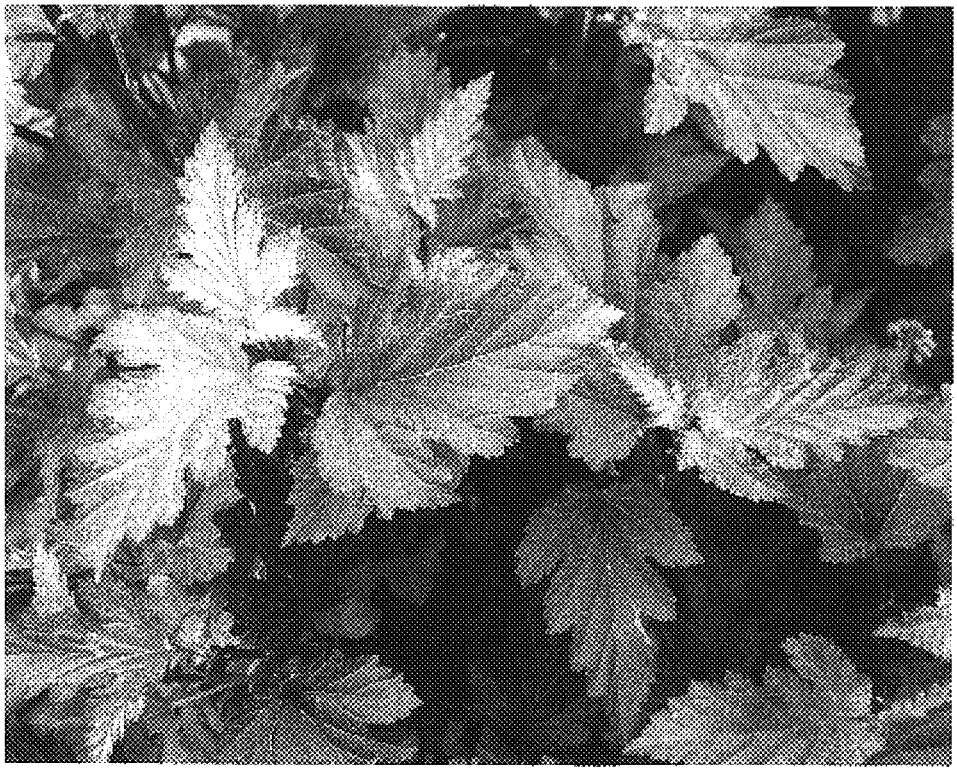

The photograph in FIG. 2 was taken in June and comprises a close-up view of the foliage of 'Center Glow'.

Figure 3:
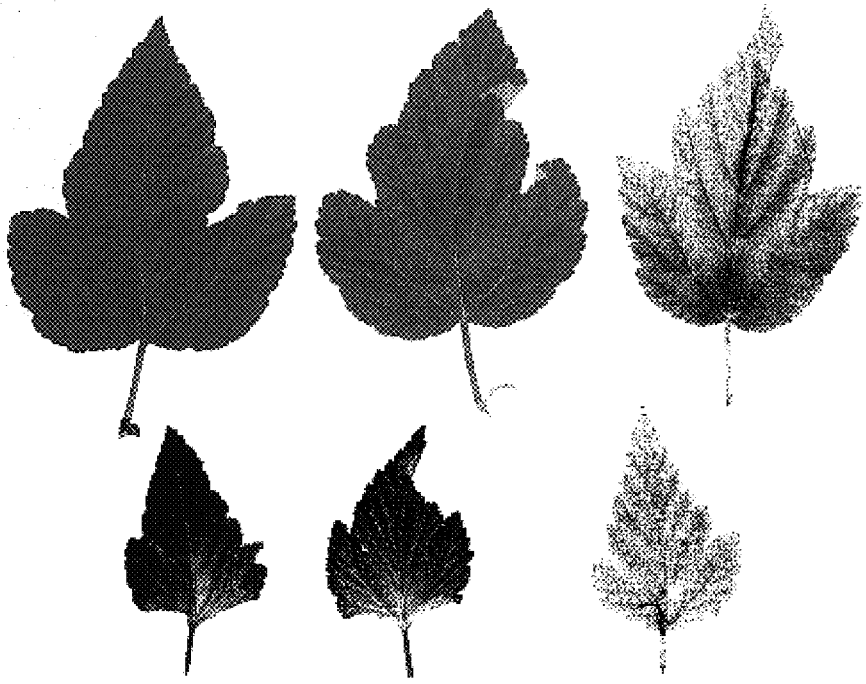

FIG. 3 is a photograph taken in July that provides a comparison between typical leaves of 'monlo' (left), 'Center Glow' (center), and 'Dart's Gold' (right) with mature leaves on the upper row and young leaves on the bottom row. The colors in the photograph are as close as possible with conventional photography and the color values given in the botanical description most closely describe the new cultivar.

BOTANICAL DESCRIPTION OF THE PLANT

The following is a detailed description of a two year-old plant of the new cultivar as grown outdoors in a trial plot in Mound, Minn. Phenotypic differences may be observed with variations in environmental, climatic, and cultural conditions. The color determination is in accordance with the 2001 R.H.S. Colour Chart of The Royal Horticultural Society, London, England, except where general color terms of ordinary dictionary significance are used.

Botanical classification: 'Center Glow' is a cultivar of *Physocarpus opulifolius.*

Parentage:

*Female parent.*—*Physocarpus opulifolius* 'monlo' disclosed in U.S. Plant Pat. No. 11,211.

*Male parent.*—*Physocarpus opulifolius* 'Dart's Gold', not patented.

General description:

*Plant habit.*—Upright, mounded, vase-shaped, deciduous shrub.

*Growth habit.*—Vigorous, densely foliated, primarily basal branches.

*Blooming period.*—About 14 to 20 days in mid June to early July.

*Height and spread.*—1.8 to 2.5 m (6 to 8 ft) in height and spread.

*Hardiness.*—USDA Zone 3.

*Diseases and pest resistance.*—No susceptibility or resistance to diseases or pests known to effect *Physocarpus opulifolius* has been observed for 'Center Glow'.

*Root description.*—Fibrous, well-developed.

Growth and propagation:

*Propagation.*—Softwood stem cuttings.

*Root initiation.*—In 3 to 4 weeks when grown during summer in a greenhouse under intermittent mist without supplemental lighting.

*Time required for root development.*—4 to 6 inch rooted cuttings will fully develop in a 2 inch container within 45 days.

Branch description:

*Branch color.*—New wood 183A, Mature wood 165A to 165C.

*Branch size.*—Up to 1 cm in diameter (average of 0.5 cm), up to 2 m in height.

*Branch surface.*—Glabrous, smooth, slight sheen.

*Internode length.*—3 to 8 cm, average 4 cm.

*Branch habit.*—Primarily densely foliaged basal branches, potential for lateral branches any node if pruned.

Foliage description:

*Leaf shape.*—Ovate in outline, deeply tri-lobed, maple-like.

*Leaf division.*—Simple.

*Leaf base.*—Cordate.

*Leaf apex.*—Acute.

*Leaf venation.*—Palmate, conspicuous, color on mature leaves; upper surface 165C, lower surface 160C, color on young leaves; upper surface 143B near base, 1B towards apex, lower surface 160A.

*Leaf margin.*—Tri-lobed, with secondary undulations, all edges are serrated.

*Leaf attachment.*—Petiolate.

*Leaf arrangement.*—Alternate.

*Leaf surface.*—Glabrous on upper and lower surfaces.

*Leaf length.*—Up to about 9.5 cm (average 8.5 cm).

*Leaf width.*—Up to about 9 cm (average 7 cm).

*Leaf number.*—About 20 to 30 per branch.

*Leaf color.*—Emerging foliage: Upper; 144B at base, center is 7A with margins of N34 and tip a color between 183A and 166A, leave gradually becomes more infused with N34, Lower; 144A at base gradually turning to 166B then 166A near apex, Young foliage: Upper; color between 166A and 183A but slightly darker. Lower; 144A with overlay of 166A, Mature: Upper; 200B, Lower; 146B.

*Petiole size.*—About 2 cm in length, about 2 mm in width.

*Petiole shape.*—Sulcate.

*Petiole color.*—183A.

*Petiole texture.*—Glabrous.

*Stipules.*—2 parted, up to 1 cm in length and 2 mm in width, 137B in color.

Flower description:

*Flower type.*—Small rotate flowers arranged in spherical corymb.

*Flower fragrance.*—Slight.

*Flower lastingness.*—Corymb lasts about Average of 14 to 20 days, not persistent, individual flowers about 3 days.

*Flower bud description.*—Elliptic in shape, average of 3.5 cm in length and 3 mm in diameter, 65D in color.

*Flower quantity.*—About 40 to 50 flowers per corymb.

*Flower size.*—About 6 mm in depth, 8 mm in diameter.

*Peduncles.*—About 1.5 cm in length and 1.5 mm in diameter, 144A in color.

*Petal description.*—5, elliptic to obovate in shape, margin is entire, apex is broadly acute, lower and upper surface is glabrous, apex is obtuse, base is attenuate.

*Petal size.*—About 5 mm in length and 4 mm in width.

*Petal color.*—Opening; upper surface 158D, lower 158D with tinge of 65C, Fully open; upper and lower surface 155D turning slightly greyer as they age.

*Calyx size.*—Average of 8 mm in length and diameter.

*Sepal description.*—5, subulate in shape, margin is entire, apex is acute, surface is glabrous.

*Sepal size.*—Average of 1.8 cm in length, 3 mm in width.

*Sepal color.*—Outer and inner surfaces; 144A when developing, turning to 75B after anthesis.

Reproductive organs:

*Gynoecium.*—4, Pistil about 0.5 mm in length, stigma is globular in shape and 145B in color, style is about 0.4 mm in length and 145B in color, ovary is 145B in color.

*Androecium.*—Numerous, anthers are oblong in shape, about 0.5 mm in length and 46A in color, pollen is scarce and 46A in color.

*Fruit and seed.*—Fruit a firm-walled inflated follicle, splitting open at both seams, 2 to 4 seeds are hard, shiny, ovoid in shape, red in color as they start developing and turning brown at maturity.

I claim:

1. A new and distinct cultivar of *Physocarpus* plant named 'Center Glow' substantially as herein illustrated and described.

* * * * *